United States Patent
Kim et al.

(10) Patent No.: US 9,889,314 B2
(45) Date of Patent: Feb. 13, 2018

(54) COLOR LIGHT THERAPY DEVICE

(75) Inventors: Nam Gyun Kim, Jeonbuk (KR); Kyong Jun Park, Seoul (KR)

(73) Assignee: COLOR SEVEN CO., LTD., Seoul (KR)

( * ) Notice: Subject to any disclaimer, the term of this patent is extended or adjusted under 35 U.S.C. 154(b) by 925 days.

(21) Appl. No.: 14/122,159

(22) PCT Filed: Dec. 2, 2011

(86) PCT No.: PCT/KR2011/009288
§ 371 (c)(1),
(2), (4) Date: Nov. 25, 2013

(87) PCT Pub. No.: WO2012/161394
PCT Pub. Date: Nov. 29, 2012

(65) Prior Publication Data
US 2014/0088668 A1    Mar. 27, 2014

(30) Foreign Application Priority Data
May 25, 2011    (KR) .......................... 10-2011-0049395

(51) Int. Cl.
*A61N 5/06*    (2006.01)
*A61H 9/00*    (2006.01)

(52) U.S. Cl.
CPC ............. *A61N 5/06* (2013.01); *A61N 5/0618* (2013.01); *A61H 2009/0064* (2013.01); *A61N 2005/0643* (2013.01); *A61N 2005/0663* (2013.01)

(58) Field of Classification Search
CPC .................... A61N 5/06; A61N 5/0616; A61N 2005/0632; A61N 2005/0643;
(Continued)

(56) References Cited

U.S. PATENT DOCUMENTS 5,259,380 A * 11/1993 Mendes ............... A61N 5/0616
606/2
5,843,143 A * 12/1998 Whitehurst ........... A61N 5/062
250/504 R
(Continued)

FOREIGN PATENT DOCUMENTS

JP    11-267178 A    10/1999
KR    20-0249062 Y1    10/2001
(Continued)

*Primary Examiner* — Ahmed Farah
(74) *Attorney, Agent, or Firm* — Rabin & Berdo, P.C.

(57) ABSTRACT

Provided is a color light therapy device. The color light therapy device includes: a body that is used by being attached to a color light therapy portion of a human body by using a double-sided adhesive tape, a hydrogel pad, or an air suction plate, and includes a printed circuit board (PCB) that supplies driving power to a light source that emits color light in a given wavelength range to perform color light therapy on the human body; and a power jack that is connected to the PCB of the body through an electric wire. Since a user may use the color light therapy device by connecting the power jack to a mobile phone, a PC, a laptop, a tablet PC, a smartphone, a personal digital assistant (PDA), a vehicle, or a socket at home while carrying the color light therapy device, anyone may conveniently use the color light therapy device to perform color light therapy on the human body without exchanging or charging a battery.

18 Claims, 12 Drawing Sheets

(58) Field of Classification Search
CPC ...... A61N 2005/0644; A61N 2005/065; A61N 2005/0651; A61N 2005/0652; A61N 2005/0653; A61N 2005/0662; A61N 2005/0663; A61N 2005/0664; A61N 2005/0665; A61N 2005/0667
USPC ........................ 607/88–91, 96, 108; 128/898
See application file for complete search history.

(56) References Cited

U.S. PATENT DOCUMENTS

| | | | | |
|---|---|---|---|---|
| 6,280,438 | B1* | 8/2001 | Eckhouse | A61B 18/203 606/9 |
| 6,290,713 | B1* | 9/2001 | Russell | A61N 5/0616 607/88 |
| 6,471,716 | B1 | 10/2002 | Pecukonis | |
| 6,558,411 | B1* | 5/2003 | Steen | A61N 5/062 606/9 |
| 6,602,275 | B1* | 8/2003 | Sullivan | A61N 5/0616 606/10 |
| 6,702,837 | B2* | 3/2004 | Gutwein | A61N 5/0616 606/9 |
| 6,860,896 | B2* | 3/2005 | Leber | A61N 5/0619 128/898 |
| 6,955,684 | B2* | 10/2005 | Savage, Jr. | A61N 5/0618 607/88 |
| 7,534,255 | B1* | 5/2009 | Streeter | A61N 5/0618 128/898 |
| 7,993,381 | B2* | 8/2011 | Mac | A61N 5/0619 128/907 |
| 2004/0106968 | A1* | 6/2004 | Yamada | A61N 5/0613 607/88 |
| 2004/0116983 | A1* | 6/2004 | Karni | A61B 18/203 607/88 |
| 2004/0225339 | A1* | 11/2004 | Yaroslavsky | A61N 5/0616 607/88 |
| 2014/0046409 | A1* | 2/2014 | Kang | F21V 9/08 607/89 |

FOREIGN PATENT DOCUMENTS

| | | |
|---|---|---|
| KR | 20-0254862 Y1 | 12/2001 |
| KR | 20-0405265 Y1 | 1/2006 |
| KR | 10-2010-0109600 A | 10/2010 |
| KR | 20-2010-0010766 U | 11/2010 |

* cited by examiner

COLOR LIGHT THERAPY DEVICE

CROSS-REFERENCE TO RELATED APPLICATION

Background

1. Field of the Invention

The present invention relates to color light therapy technology, and more particularly, to a color light therapy device that emits color light in a given wavelength range in order to intensively perform color light therapy to a portion of a human body.

2. Discussion of Related Art

Color light therapy is known as the act of helping to cure a disease or manage health by stimulating a human body with energy of various pieces of color light having unique wavelengths, and is widely used for anti-fatigue and skin care purposes or for alternative treatment and rehabilitation treatment purposes.

Actually, various types of color light therapy have recently been performed to treat an affected part, treat a specific body part associated with an acupuncture point by stimulating the acupuncture point at and through which qi-blood gathers around a body surface and passes, treat atopic dermatitis, treat pain or inflammation (for example, menstrual pain or burns), prevent and treat a stroke and dementia, or improve health by using energy of color light in medicine, oriental medicine, or alternative medicine.

As a conventional color light therapy device used to perform color light therapy, a portable color therapy device (Korean Utility Model Registration No. 20-0249062, registered on 21 Sep. 2001) and a portable color therapy device (Korean Utility Model Registration No. 20-0254862, registered on 8 Nov. 2001) have been developed. Each of the portable color therapy devices is carried in a user's hand and is configured to emit unique color light by using a color filter that may be exchanged with a white light-emitting diode (LED).

Also, a light irradiation device for medical treatment using an LED (Korean Utility Model Registration No. 20-0405265, registered on 29 Dec. 2005) promotes the natural healing power of an affected part by emitting LED light that may cure a human body and select a wavelength range according to a patient's symptom for biostimulation effects.

However, the light irradiation device for medical treatment using the LED (Korean Utility Model Registration No. 20-0405265, registered on 29 Dec. 2005) has problems in that since color light is widely irradiated to the affected part by applying the light irradiation device in the form of a mat, an ordinary person may not easily purchase and use the light irradiation device anywhere, and particularly, a user may not intensively irradiate and use color light to a specific acupuncture point of a human body.

Also, each of the portable color therapy device (Korean Utility Model Registration No. 20-0249062, registered on 21 Sep. 2001) and the portable color therapy device (Korean Utility Model Registration No. 20-0254862, registered on 8 Nov. 2001) has problems in that since only the white LED is used, the color filter has to be replaced in order to obtain desired color light, and particularly, the user has to use the color therapy device by holding it in his/her hand.

SUMMARY OF THE INVENTION

The present invention is directed to a color light therapy device including a body that is used by being attached to a portion of a human body by using a double-sided adhesive tape, a hydrogel pad, or an air suction plate and includes a printed circuit board (PCB) that supplies driving power to a light source (for example, a light-emitting diode (LED), an organic light-emitting diode (OLED), or a tricolor LED that may generate various pieces of color light) for emitting color light (for example, orange light, red light, green light, or yellow light) in a given wavelength range (for example, a visible light wavelength band ranging from 400 nm to 800 nm in which color light is visible at a point of time when the color light touches skin) to perform color light therapy on the human body, and a power jack that is connected to the PCB of the body through an electric wire, wherein the color light therapy is performed by intensively irradiating the color light for treatment to the color light therapy portion of the human body through a light outlet that is formed in a front portion of the body.

The present invention is also directed to the color light therapy device that emits color light emitted by a plurality of light sources through the light outlet that is formed in the front portion of the body in order to intensively irradiate the color light for treatment to the color light therapy portion of the human body.

The present invention is also directed to the color light therapy device further including an optical filter that is provided on the PCB that is received in the body, is formed of plastic, glass, quartz, crystal, or crystal glass, is configured such that a light-transmitting surface is cut to have a circular or polygonal shape (for example, a pentagonal shape, a hexagonal shape, or an octagonal shape) or has a planar or convex lens shape, and filters and focuses the color light emitted by the light source and emits the filtered and focused color light through the light outlet.

The present invention is also directed to the color light therapy device further including a reflector that is provided around the light source that is provided on the PCB that is received in the body, is formed of a reflection plate or a reflection film, and reflects the color light emitted by the light source to the light outlet.

The present invention is also directed to the color light therapy device that is configured such that a plurality of the bodies are connected to one power jack through the electric wire.

The present invention is also directed to the color light therapy device that is configured such that a gender for separation/connection that may separate or connect the body and the power jack is provided on the electric wire.

The present invention is also directed to the color light therapy device further including a light source operation button that is provided to be exposed to the outside of the body, is connected to the PCB that is received in the body, and repeatedly outputs a light source ON signal and a light source OFF signal whenever being pressed once.

The present invention is also directed to the color light therapy device further including a light source operation controller that is provided to be exposed to the outside of the body or is provided on the electric wire that connects the body and the power jack, is connected to the PCB that is received in the body, and includes only a light source operation button that repeatedly outputs a light source ON signal and a light source OFF signal whenever being pressed once or includes at least one of a light source pattern button that repeatedly outputs a continuous light source pattern selection signal and a discontinuous light source pattern selection signal whenever being pressed once along with the light source operation button, a time adjustment button that adjusts a light source operation time, and a brightness adjustment button that adjusts light source brightness.

According to an aspect of the present invention, there is provided a color light therapy device including: a printed circuit board (PCB) on which at least one of a light-emitting diode (LED), an organic light-emitting diode (OLED), and a tricolor LED that may generate various pieces of color light is provided as a light source for emitting color light (for example, orange light, red light, green light, or yellow light) in a given wavelength range (for example, a visible light wavelength band ranging from 400 nm to 800 nm in which the color light is visible at a point of time when the color light touches skin) to perform color light therapy on a human body and that supplies driving power to the light source; and a body in which the PCB is received and that has a front portion in which a light outlet for intensively irradiating color light for treatment to a color light therapy portion of the human body; and a power jack that is connected to the PCB that is received in the body through an electric wire.

A wavelength range of the color light that is emitted by the light source for color light therapy through the light outlet of the body may be a visible light wavelength band in which the color light is visible at a point of time when the color light touches skin.

The color light therapy device may further include an optical filter that is provided on the PCB that is received in the body, is formed of any one of plastic, glass, quartz, crystal, and crystal glass, is configured such that a light-transmitting surface is cut to have a circular or polygonal shape (for example, a pentagonal shape, a hexagonal shape, or an octagonal shape) or has a planar or convex lens shape, and filters and focuses the color light emitted by the light source and emits the filtered and focused color light through the light outlet.

The color light therapy device may further include a reflector that is provided around the light source that is provided on the PCB that is received in the body, is formed of any one of a reflection plate and a reflection film, and reflects the color light emitted by the light source to the light outlet.

At least one body may be connected to one power jack through the electric wire.

A gender for separation/connection that may separate or connect the body and the power jack may be provided on the electric wire.

The body may be used by being attached to the color light therapy portion of the human body by using a double-sided adhesive tape, a hydrogel pad, or an air suction plate.

The color light therapy device may further include a light source operation button that is provided to be exposed to the outside of the body, is connected to the PCB that is received in the body, and repeatedly outputs a light source ON signal and a light source OFF signal whenever being pressed once.

The color light therapy device may further include a light source operation controller that is provided to be exposed to the outside of the body or is provided on the electric wire that connects the body and the power jack, is connected to the PCB that is received in the body, and includes only a light source operation button that repeatedly outputs a light source ON signal and a light source OFF signal whenever being pressed once or at least one of a light source pattern button that repeatedly outputs a continuous light source pattern selection signal and a discontinuous light source pattern selection signal whenever being pressed once along with the light source operation button, a time adjustment button that adjusts a light source operation time, and a brightness adjustment button that adjusts light source brightness.

BRIEF DESCRIPTION OF THE DRAWINGS

The above and other objects, features, and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

The present invention will now be described more fully with reference to the accompanying drawings, in which exemplary embodiments of the invention are shown.

Figure 1:
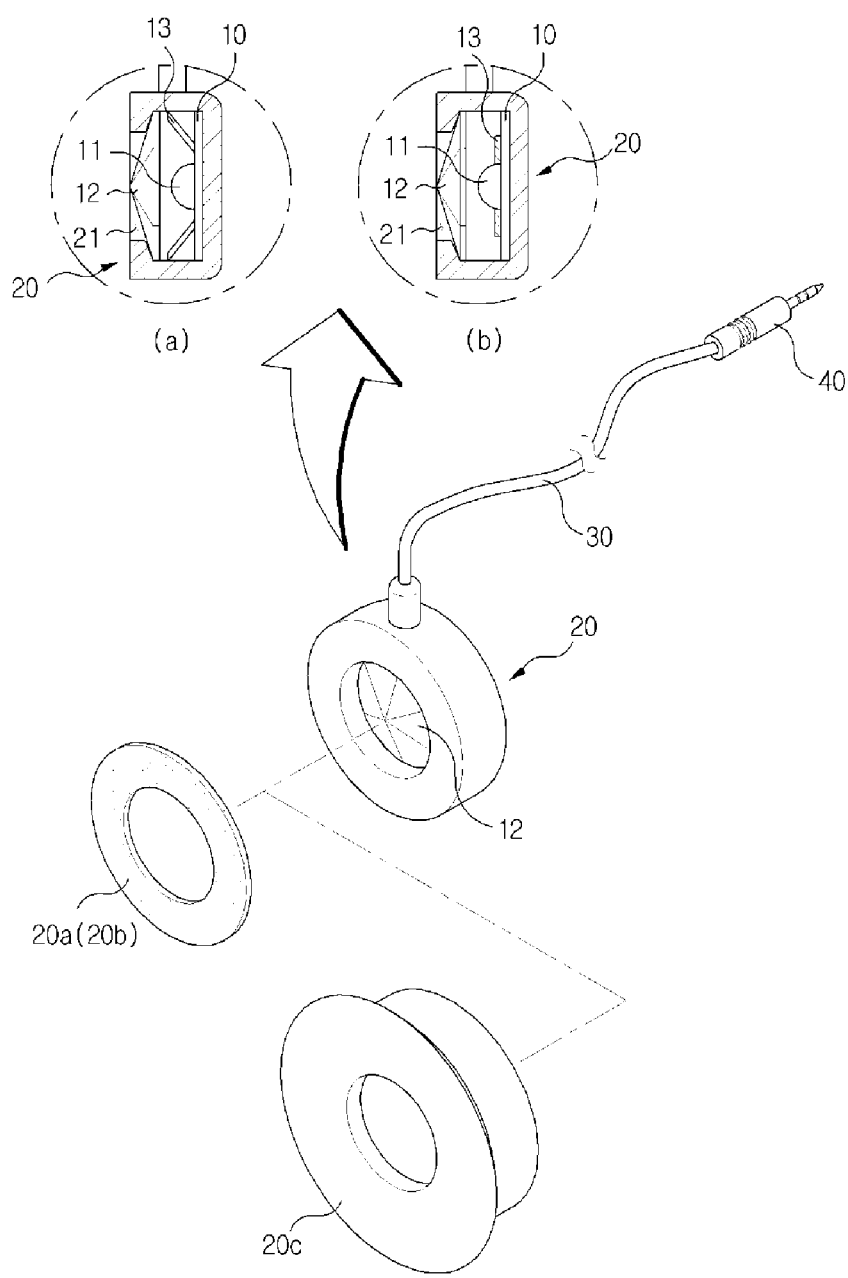
FIG. 1 is a view illustrating a cylindrical color light therapy device using one light source, according to an embodiment of the present invention.
Figure 2:
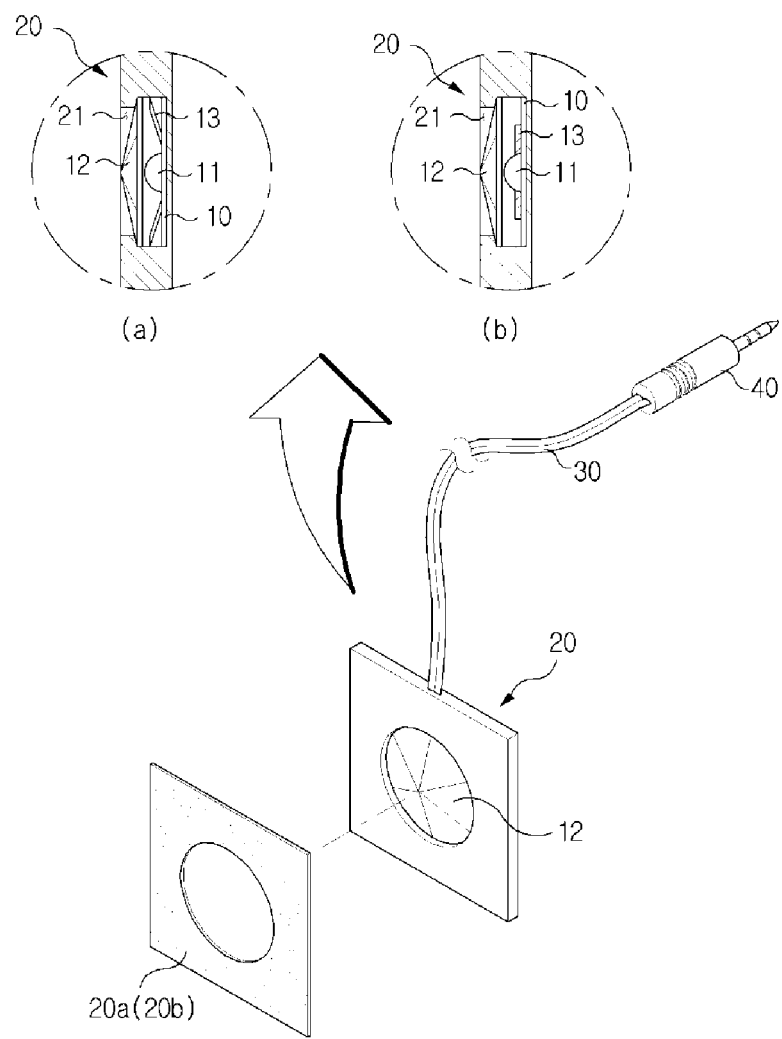
FIG. 2 is a view illustrating a patch-type color light therapy device using one light source, according to an embodiment of the present invention.

FIG. 1 is a view illustrating a cylindrical color light therapy device using one light source 11, according to an embodiment of the present invention. FIG. 2 is a view illustrating a patch-type color light therapy device using one light source 11, according to an embodiment of the present invention.

Referring to FIGS. 1 and 2, the color light therapy device includes a printed circuit board (PCB) 10 on which the light source 11 is provided, a body 20 in which the PCB 10 is received, and a power jack 40 that is connected to the body 20 through an electric wire 30.

At least one of a light-emitting diode (LED), an organic light-emitting diode (OLED), or a tricolor LED that may generate various pieces of color light is provided on the PCB 10 as the light source 11 that emits colorelight (for example, orange light, red light, green light, or yellow light) in a given wavelength range (for example, a visible light wavelength band ranging from 400 nm to 800 nm in which color light is visible at a point of time when the color light touches skin) to perform color light therapy on a human body, and the PCB 10 supplies driving power to the light source 11.

An optical filter 12 that is formed of plastic, glass, quartz, crystal, or crystal glass, is configured such that a light-transmitting surface is cut to have a circular or polygonal shape (for example, a pentagonal shape, a hexagonal shape, or an octagonal shape) or has a planar or convex lens shape, and filters and focuses the color light emitted by the light source 11 and emits the filtered and focused color light through a light outlet 21 is further provided on the PCB 10, as shown in (a) and (b) of FIGS. 1 and 2. For reference, an LED illumination unit such as an LED, an OLED, or a tricolor LED used as the light source 11 is theoretically an illumination unit having a single wavelength but actually has a wide bandwidth instead of a single wavelength because of a wide frequency spectrum width. When the optical filter 12 having a frequency similar to a single frequency desired from the LED illumination unit is used in order to obtain a single frequency spectrum component, part of light emitted by the LED illumination unit is resonance-absorbed and light having the same frequency component as that of the optical filter 12 is selectively emitted.

A reflector 13 that is formed of a reflection plate or a reflection film and reflects the color light emitted by the light source 11 to the light outlet 21 is further provided around the light source 11 that is provided on the PCB 10, as shown in (a) and (b) of FIGS. 1 and 2.

The PCB 10 is received in the body 20, and the light outlet 21 for intensively irradiating the color light for treatment to a color light therapy portion of the human body is formed in a front portion of the body 20.

The body 20 may be formed to have a cylindrical shape as shown in FIG. 1 or may be formed as a patch-type as shown in FIG. 2, but if necessary, may be formed to have any of various shapes such as a hemispheric shape, a jar shape, an elliptical shape, and a heart shape.

The body 20 is used by being attached to the color light therapy portion of the human body by using a double-sided adhesive tape 20a, a hydrogel pad 20b, or an air suction plate 20c. For reference, FIG. 1 illustrates a case where the body 20 having a cylindrical shape is attached to the color light therapy portion of the human body by using the double-sided adhesive tape 20a, the hydrogel pad 20b, or the air suction plate 20c, and FIG. 2 illustrates a case where the body 20 is attached as a patch-type to the color light therapy portion of the human body by using the double-sided adhesive tape 20a or the hydrogel pad 20b.

The power jack 40 is connected to the PCB 10 that is received in the body 20 through the electric wire 30.

The power jack 40 may be any jack as long as a user may use the color light therapy device by connecting the power jack 40 to a mobile phone, a PC, a laptop, a tablet PC, a smartphone, a personal digital assistant (PDA), a vehicle, or a socket at home. For example, the power jack 40 may be a universal serial bus (USB) jack that may be used by being connected to a mobile phone, a PC, a laptop, a tablet PC, a smartphone, or a PDA, a charger jack such as a 5-pin jack, a 20-pin jack, a 24-pin jack, or a 30-pin jack that may be used by being connected to a mobile phone, a PC, a laptop, a tablet PC, a smartphone, or a PDA, or a combined power/data jack, an audio and video input/output jack, a car cigar jack, a plug that is connected to a socket at home, or an alternating current/direct current (AC/DC) adaptor jack.

Figure 3:
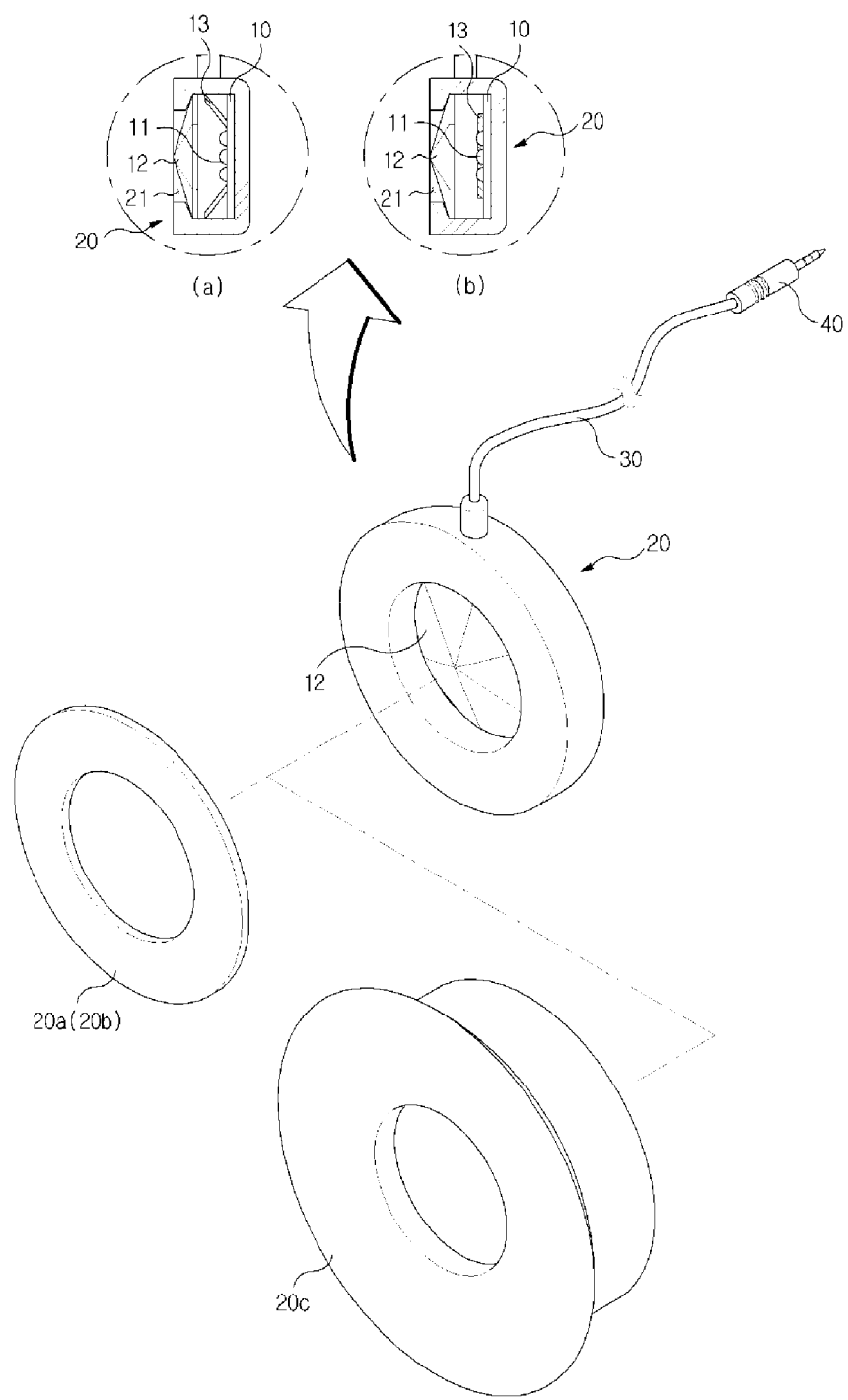
FIG. 3 is a view illustrating a cylindrical color light therapy device using a plurality of light sources, according to an embodiment of the present invention.
Figure 4:
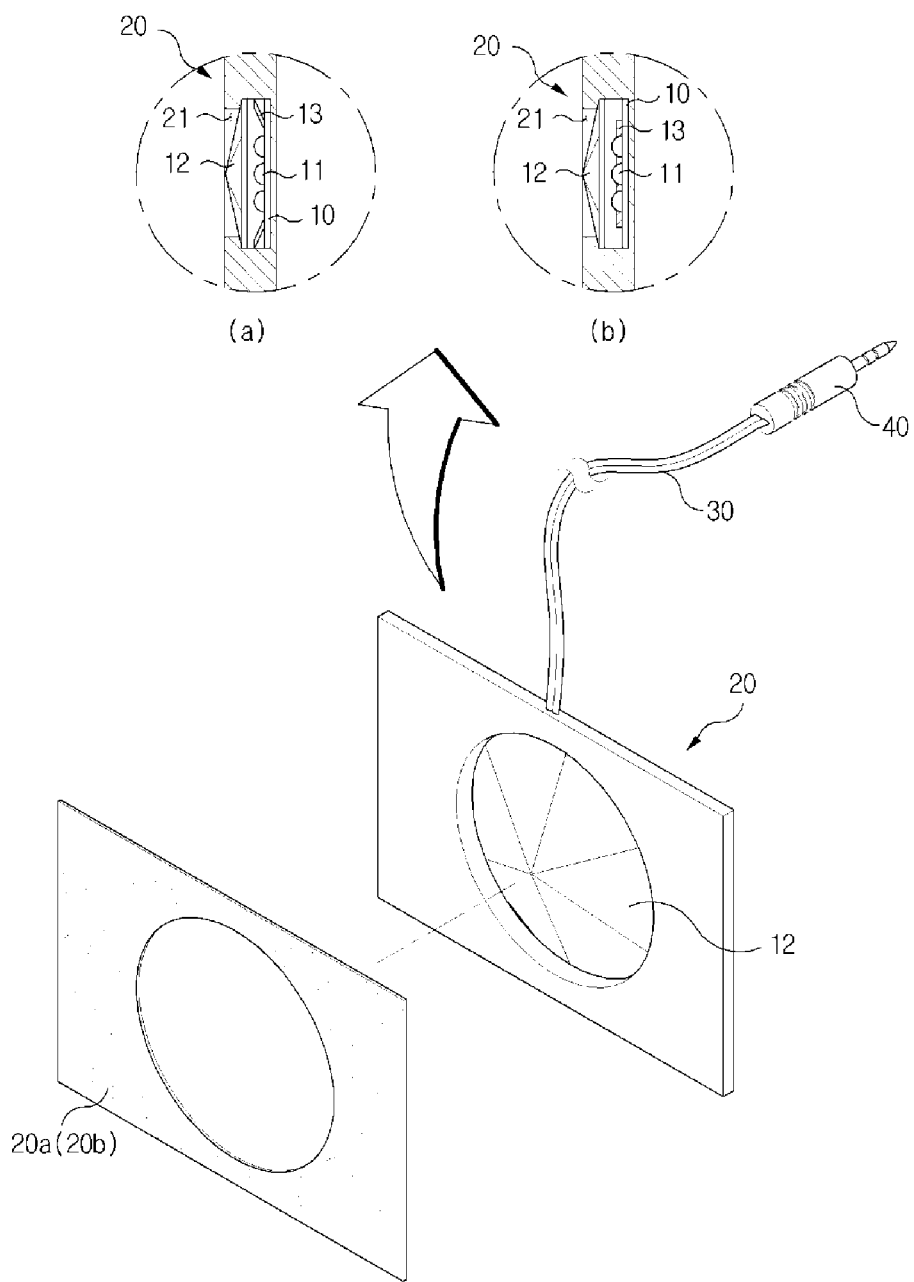
FIG. 4 is a view illustrating a patch-type color light therapy device using the plurality of light sources, according to an embodiment of the present invention.

FIG. 3 is a view illustrating a cylindrical color light therapy device using a plurality of light sources 11, according to an embodiment of the present invention. FIG. 4 is a view illustrating a patch-type color light therapy device using the plurality of light sources 11, according to an embodiment of the present invention.

Referring to FIGS. 3 and 4, the color light therapy device may enable the plurality of light sources 11 to emit color light through the light outlet 21 that is formed in the front portion of the body 20 in order to intensively irradiate the color light for treatment over the color light therapy portion of the human body.

Also, as shown in (a) and (b) of FIGS. 3 and 4, the optical filter 12 that filters and focuses the color light emitted by the plurality of light sources 11 and emits the filtered and focused color light through the light outlet 21 or the reflector 13 that is formed of a reflection plate or a reflection film and reflects the color light emitted by the plurality of light sources 11 to the light outlet 21 is provided on the PCB 10 on which the plurality of light sources 11 are provided.

Figure 5:
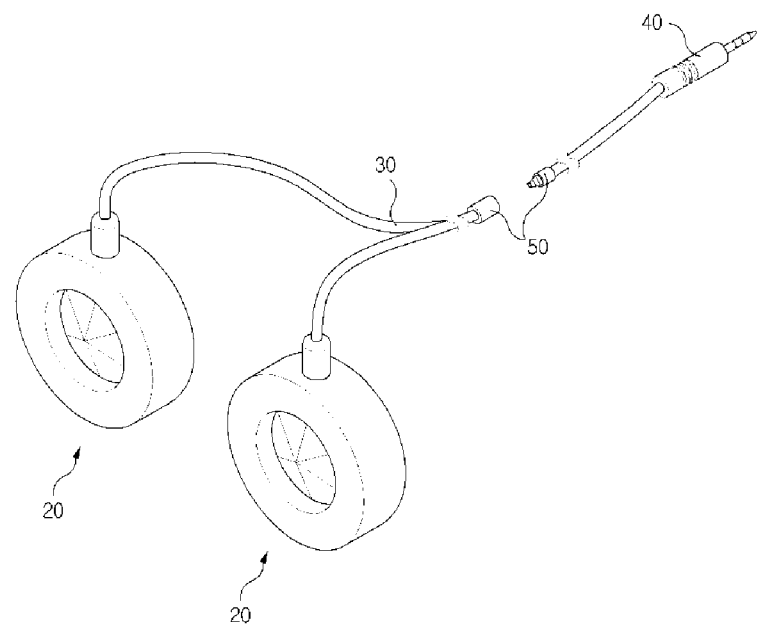
FIG. 5 is a view illustrating a cylindrical color light therapy device including a plurality of bodies, according to an embodiment of the present invention.
Figure 6:
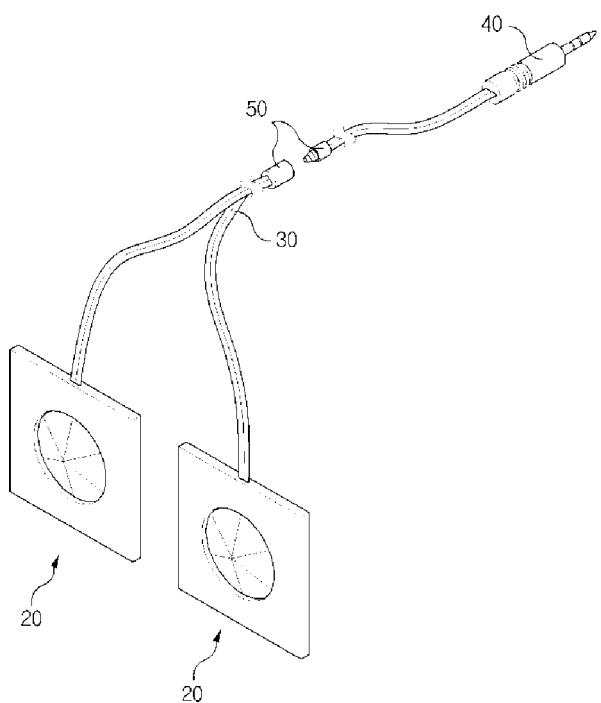
FIG. 6 is a view illustrating a patch-type color light therapy device including the plurality of bodies, according to an embodiment of the present invention.

FIG. 5 is a view illustrating a cylindrical color light therapy device including a plurality of bodies 20, according to an embodiment of the present invention. FIG. 6 is a view illustrating a patch-type color light therapy device including the plurality of bodies 20, according to an embodiment of the present invention.

Referring to FIGS. 5 and 6, at least one, that is, one or more bodies 20 are connected to one power jack 40 through the electric wire 30.

As shown in FIGS. 5 and 6, a gender 50 for separation/connection that may separate or connect the bodies 20 and the power jack 40 may be provided on the electric wire 30.

Figure 7:
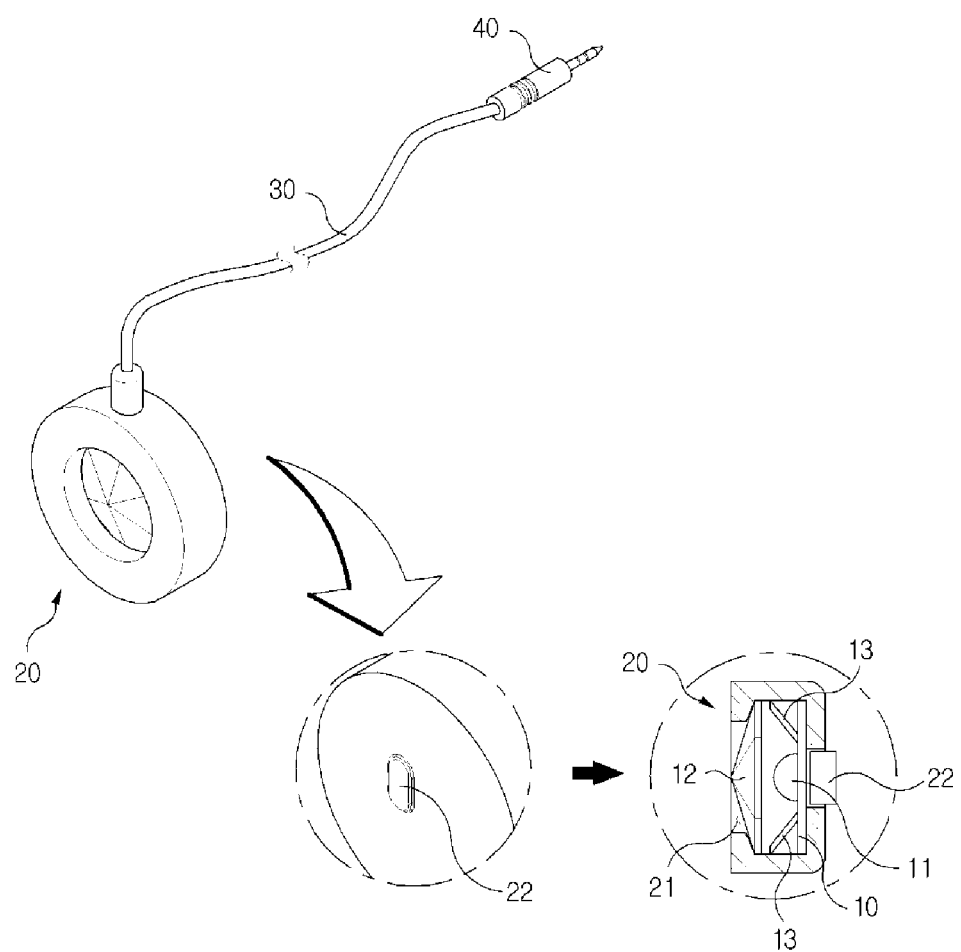
FIG. 7 is a view illustrating a cylindrical color light therapy device including a body on which a light source operation button is provided, according to an embodiment of the present invention.
Figure 8:
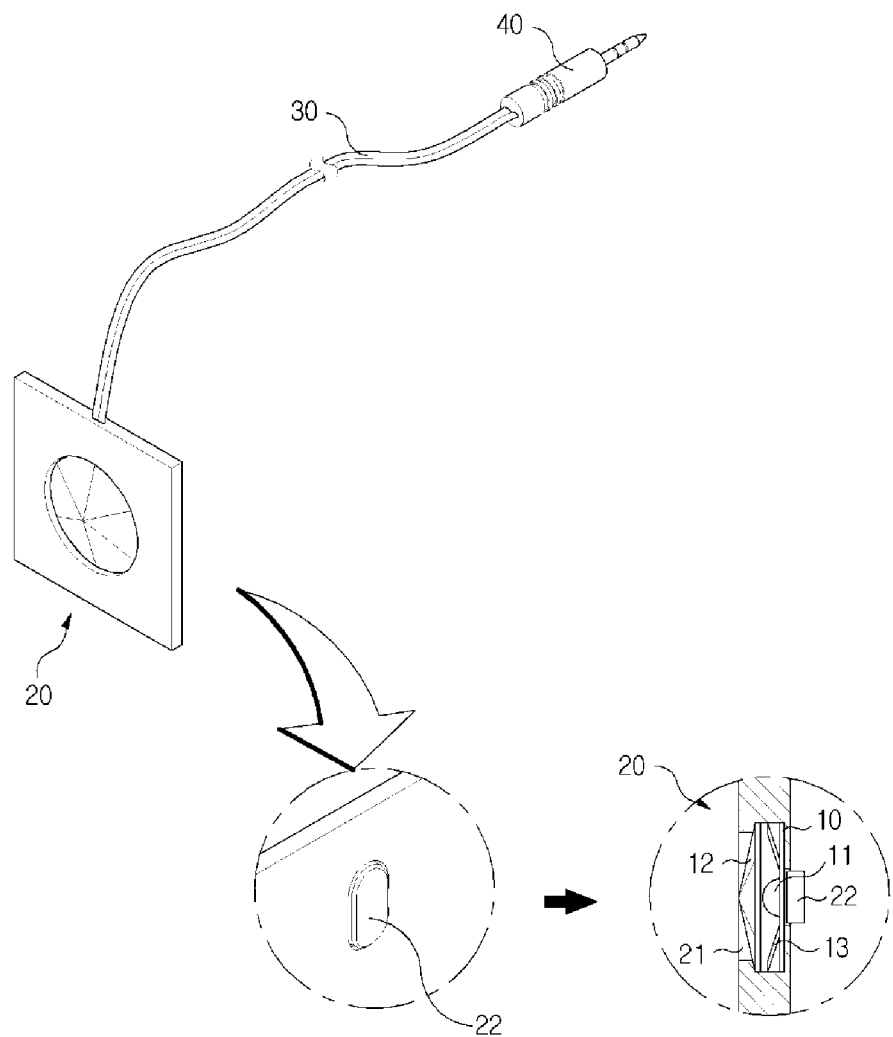
FIG. 8 is a view illustrating a patch-type color light therapy device including the body on which the light source operation button is provided, according to an embodiment of the present invention.

FIG. 7 is a view illustrating a cylindrical color light therapy device including the body 20 on which a light source operation button 22 is provided, according to an embodiment of the present invention. FIG. 8 is a view illustrating a patch-type color light therapy device including the body 20 on which the light source operation button 22 is provided, according to an embodiment of the present invention.

Referring to FIGS. 7 and 8, the color light therapy device further includes the light source operation button 22 that is provided to be exposed to the outside of the body 20, is connected to the PCB 10 that is received in the body 20, and repeatedly outputs a light source ON signal and a light source OFF signal whenever being pressed once.

Although the light source operation button 22 is provided on a rear surface of the body 20 in FIGS. 7 and 8, the light source operation button 22 may be provided on a side surface of the body 20.

Although not shown in FIGS. 7 and 8, at least one, that is, one or more bodies 20 each including the light source operation button 22, are connected to one power jack 40 through the electric wire 30. Also, the gender 50 for separation/connection that may separate or connect the bodies 20 and the power jack 40 may be provided on the electric wire 30.

Figure 9:
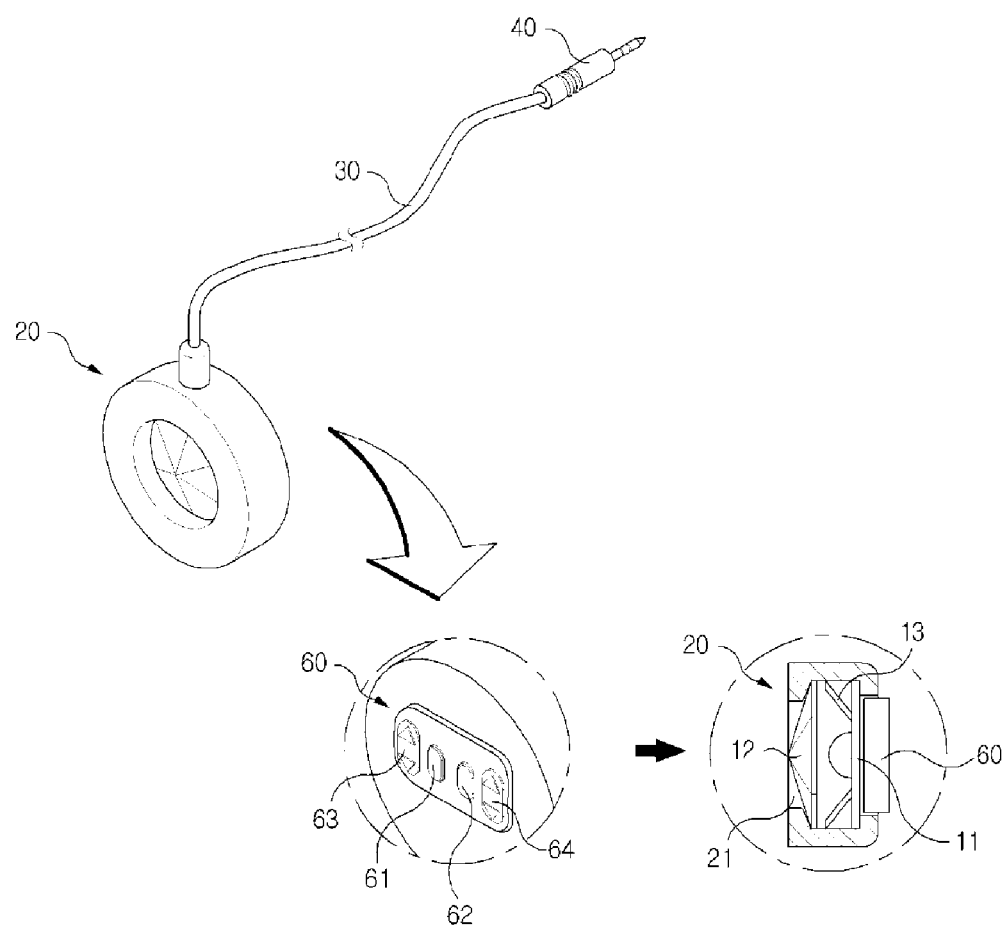
FIG. 9 is a view illustrating a cylindrical color light therapy device including a body on which a light source operation controller is provided, according to an embodiment of the present invention.
Figure 10:
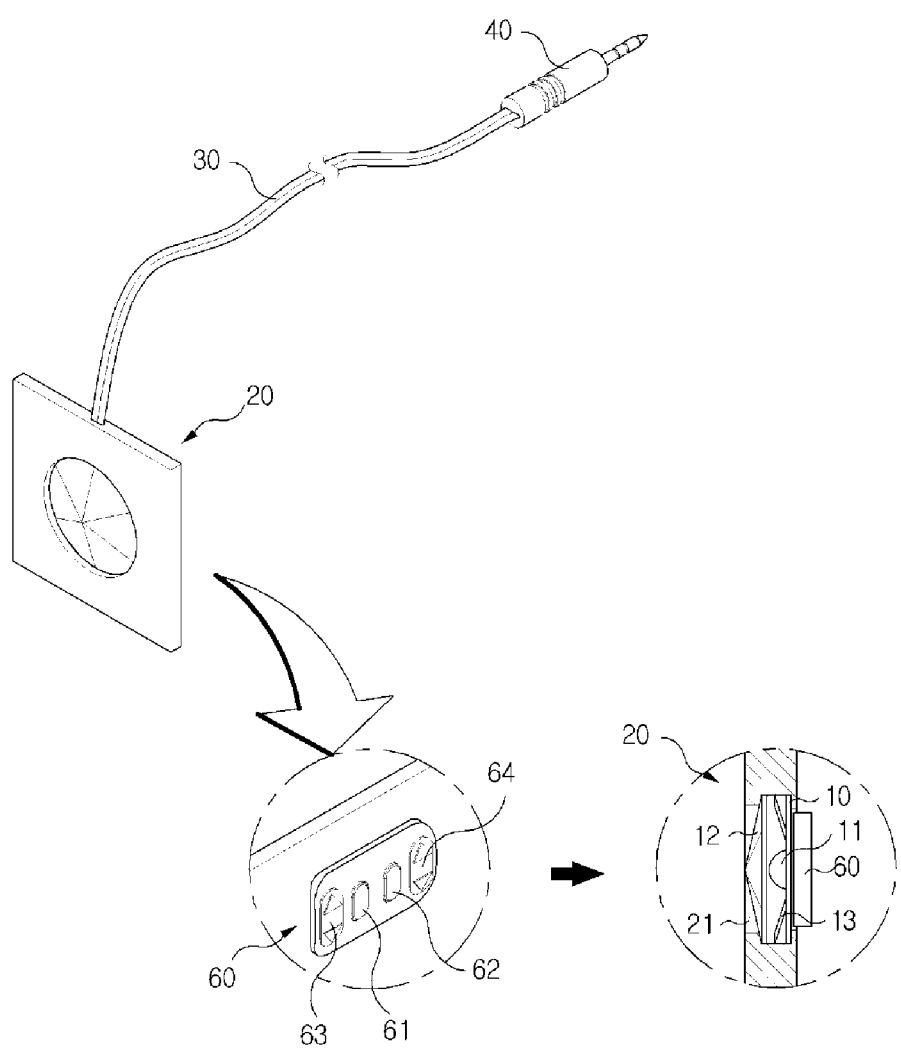
FIG. 10 is a view illustrating a patch-type color light therapy device including the body on which the light source operation controller is provided, according to an embodiment of the present invention.

FIG. 9 is a view illustrating a cylindrical color light therapy device including the body 20 on which a light source operation controller 60 is provided, according to an embodiment of the present invention. FIG. 10 is a view illustrating a patch-type color light therapy device including the body 20 on which the light source operation controller 60 is provided, according to an embodiment of the present invention.

Referring to FIGS. 9 and 10, the color light therapy device further includes the light source operation controller 60 that is provided to be exposed to the outside of the body 20, is connected to the PCB 10 that is received in the body 20, and includes only a light source operation button 61 that repeatedly outputs a light source ON signal and a light source OFF signal whenever being pressed once or includes at least one of a light source pattern button 62 that repeatedly outputs a continuous light source pattern selection signal and a discontinuous light source pattern selection signal whenever being pressed once along with the light source operation button 61, a time adjustment button 63 that adjusts a light source operation time, and a brightness adjustment button 64 that adjusts light source brightness.

Although the light source operation controller 60 is provided on a rear surface of the body 20 in FIGS. 9 and 10, the light source operation controller 60 may be provided on a side surface of the body 20.

Although not shown in FIGS. 9 and 10, at least one, that is, one or more bodies 20 each including the light source operation controller 60, are connected to one power jack 40 through the electric wire 30. Also, the gender 50 for separation/connection that may separate or connect the body 20 and the power jack 40 may be provided on the electric wire 30.

Figure 11:
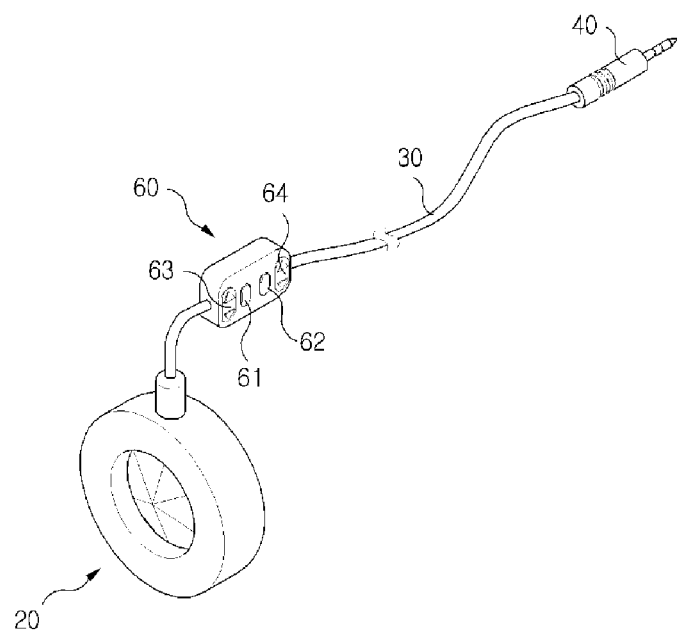
FIG. 11 is a view illustrating a cylindrical color light therapy device including an electric wire on which the light source operation controller is provided, according to an embodiment of the present invention.
Figure 12:
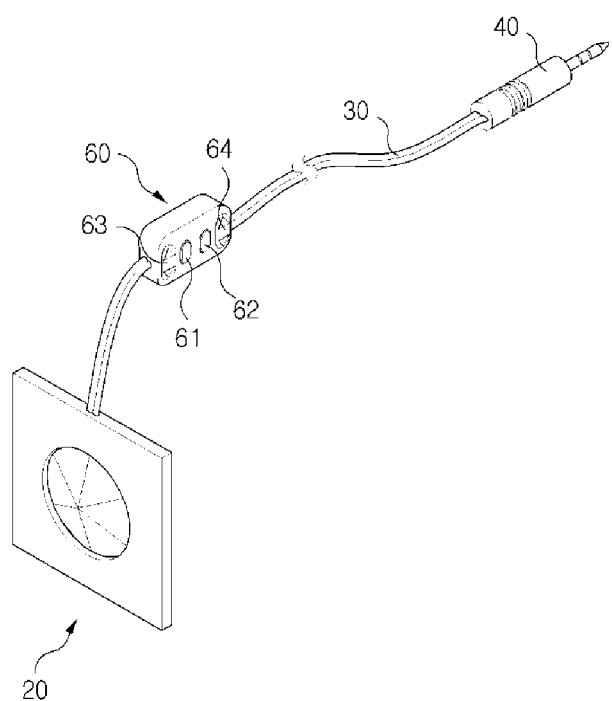
FIG. 12 is a view illustrating a patch-type color light therapy device including the electric wire on which the light source operation controller is provided, according to an embodiment of the present invention.

FIG. 11 is a view illustrating a cylindrical color light therapy device including the electric wire 30 on which the light source operation controller 60 is provided, according to an embodiment of the present invention. FIG. 12 is a view illustrating a patch-type color light therapy device including the electric wire 30 on which the light source operation controller 60 is provided, according to an embodiment of the present invention.

Referring to FIGS. 11 and 12, the color light therapy device further includes the light source operation controller 60 that is provided on the electric wire 30 that connects the body 20 and the power jack 40, is connected to the PCB 10 that is received in the body 20, and includes only the light source operation button 61 that repeatedly outputs a light source ON signal and a light source OFF signal whenever being pressed once or includes at least one of the light source pattern button 62 that repeatedly outputs a continuous light source pattern selection signal and a discontinuous light source pattern selection signal whenever being pressed once along with the light source operation button 61, the time adjustment button 63 that adjusts a light source operation time, and the brightness adjustment button 64 that adjusts light source brightness.

Although not shown in FIGS. 11 and 12, at least one, that is, one or more bodies 20 connected to the light source operation controller 60 that is provided on the electric wire 30, are connected to one power jack 40 through the electric wire 30. Also, the gender 50 for separation/connection that may separate or connect the bodies 20 and the power jack 40 may be provided on the electric wire 30.

The color light therapy device constructed as described above is used as follows.

The color light therapy device according to the present invention is used to treat an affected part, treat a specific body part associated with an acupuncture point by stimulating the acupuncture point at and through which qi-blood gathers around a body surface and passes, treat atopic dermatitis, treat pain or inflammation (for example, menstrual pain or burns), prevent and treat a stroke and dementia, or improve health by using energy of color light in medicine, oriental medicine, or alternative medicine.

Figure 13:
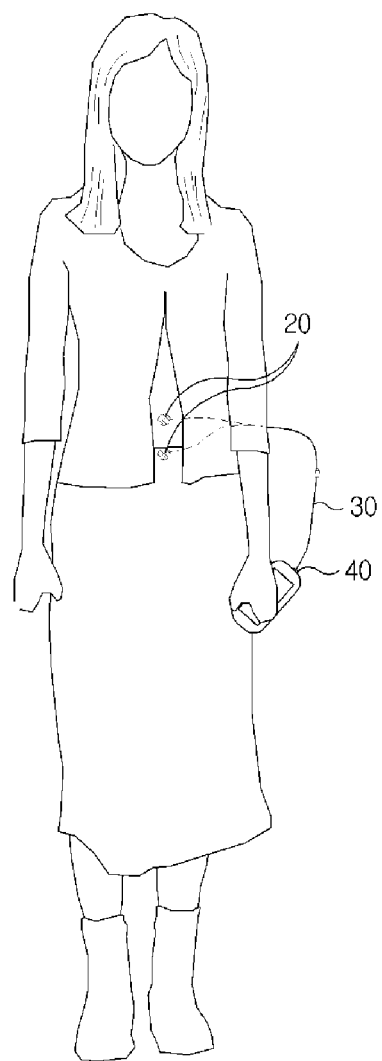
FIG. 13 is a view illustrating a state where menstrual pain treatment is performed by connecting a color light therapy device according to the present invention to a smartphone.
Figure 14:
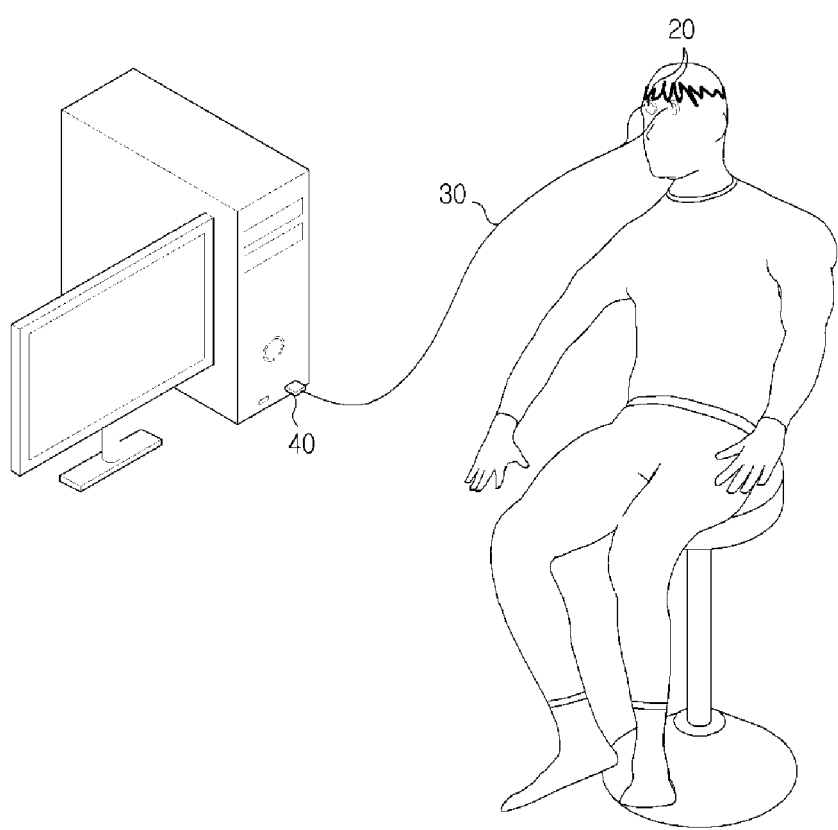
FIG. 14 is a view illustrating a state where dementia treatment is performed by connecting a color light therapy device according to the present invention to a PC.

For example, FIG. 13 is a view illustrating a state where menstrual pain treatment is performed by connecting a color light therapy device according to the present invention to a smartphone. FIG. 14 is a view illustrating a state where dementia treatment is performed by connecting a color light therapy device according to the present invention to a PC.

Referring to FIG. 13, a user uses the color light therapy device by connecting the power jack 40 that is connected to the electric wire 30 of the color light therapy device to an earphone socket or a USB terminal of the smartphone, and attaching the body 20 to a menstrual pain treatment portion (for example, a acupuncture point such as a point Ki-Hae (Conception Vessel 6, CV6) that is located several centimeters below the navel and functions to discharge carbon dioxide to the outside of the body and relieve any pain below the navel through systemic circulation and activation, or a point Jung-Wan(CV12) that is located between the navel and the solar plexus and functions to produce good energy and boost metabolism by stimulating the activity of the brain) of the human body that is said in oriental medicine to be associated with the womb by using the double-sided adhesive tape 20a, the hydrogel pad 20b, or the air suction plate 20c.

Referring to FIG. 14, the user uses the color light therapy device by connecting the power jack 40 that is connected to the electric wire 30 to an earphone socket or a USB terminal of the PC, and by attaching the body 20 to a dementia treatment portion (for example, an acupuncture point such as a point Gok-ji(CV11), a point Jung-Wan(CV12), a point Geo-Gwol(CV14), or a point Bu-Dol(CV18), a central portion of the forehead, or a neck portion in which the main artery flows to the brain) of the human body that is said in oriental medicine to be associated with dementia prevention and treatment by using the double-sided adhesive tape 20a, the hydrogel pad 20b, or the air suction pad 20c.

Assuming that the color light therapy device does not include the light source operation button 22 or the light source operation controller 60, when the user connects the power jack 40 to the smartphone or the PC, the light source 11 emits color light (for example, orange light, red light, green light, or yellow light) in a given wavelength range (for example, a visible light wavelength band ranging from 400 nm to 800 nm in which color light is visible at a point of time when the color light touches skin) to perform color light therapy on the user's body, and when the user separates the power jack 40 from the smartphone or the PC, the light source 11 is turned off.

By contrast, assuming that the color light therapy device includes the light source operation button 22 or the light source operation controller 60, when the user outputs a light source ON signal by pressing the light source operation button 22 included in the body 20 of the color light therapy device, or outputs a light source ON signal by pressing the light source operation button 61 included in the light source operation controller 60, the light source 11 emits color light.

Also, when the user outputs a light source OFF signal by pressing again the light source operation button 22 that is included in the body 20 of the color light therapy device or outputs a light source OFF signal by pressing again the light source operation button 61 that is included in the light source operation controller 60 while the light source 11 emits the color light, the light source 11 is turned off.

The color light emitted by the light source 11 of the body 20 is filtered and focused by the optical filter 12, is reflected by the reflector 13 to the light outlet 21, and is emitted through the light outlet 21, to be intensively irradiated to the menstrual pain treatment portion or the dementia treatment portion during a given period of time (for example, 10±5 minutes).

In fact, once the color light for treatment is irradiated to the menstrual pain treatment portion, photon energy is supplied to a damaged cell, metabolism of the damaged cell is boosted, circulation is promoted, and the supply of oxygen and nutrients to a damaged womb tissue is increased to relieve menstrual pain. For reference, menstrual pain treatment performed by the color light therapy device of the present invention is based on a principle that photons of light that are intensively irradiated to a menstrual pain treatment portion of a human body that is said in oriental medicine to be associated with the womb move along a meridian pathway, and react with light receptors in cells when reaching the womb, to generate nitrogen monoxide (nitric oxide (NO)), increase a cyclic adenosine monophosphate (cAMP) concentration, relax a smooth muscle constituting the womb, boost circulation, and thus increase the supply of oxygen and nutrients to the damaged womb. Even in western medicine, since a point to which colorelight is irradiated is a portion where the womb exists, the color light irradiated to skin may reach and treat the womb based on this principle.

Also, once the color light for treatment is irradiated to the dementia treatment portion of the human body, photon energy is supplied to a brain cell or tissue, to increase a cyclic adenosine monophosphate (cAMP) concentration in the brain cell or tissue, increase the generation of nitrogen monoxide (nitric oxide) by oxidative enzymes (cytochrome c oxidase), increase the supply of oxygen and nutrients to the brain cell or tissue, increase blood flow, reduce inflammation, and thus improve memory.

While the user performs menstrual pain treatment by connecting the color light therapy device to the smartphone or performs dementia treatment by connecting the color light therapy device to the PC as described in the above, when the light source pattern button 62 that is included in the light source operation controller 60 and repeatedly outputs a continuous light source pattern selection signal and a discontinuous light source pattern selection signal whenever being pressed once is manipulated, the color light emitted by the light source 11 may be continuously irradiated to the color light therapy portion of the human body or discontinuously irradiated to the menstrual pain treatment portion of the human body.

Also, while the user performs menstrual pain treatment by connecting the color light therapy device to the smartphone or performs dementia treatment by connecting the color light therapy device to the PC, when the time adjustment button 63 that is included in the light source operation controller 60 and adjusts a light source operation time is manipulated to adjust a period of time for which the color light emitted by the light source 11 is irradiated to the color light therapy portion of the human body, the color light therapy device may be performed for a desired period of time and after a preset time passes, the light source 11 may be automatically turned off.

Also, while the user performs menstrual pain treatment by connecting the color light therapy device to the smartphone or performs dementia treatment by connecting the color light therapy device to the PC, when the brightness adjustment button 64 that is included in the light source operation controller 60 and adjusts light source brightness is manipulated, brightness of the color light emitted by the light source 11 may be adjusted.

Also, when the user performs menstrual pain treatment by connecting the color light therapy device to the smartphone or performs dementia treatment by connecting the color light therapy device to the PC, only power of the smartphone or the PC may be used, or a color light therapy program that is mounted in the smartphone or the PC and provides a color light therapy user interface (UI) screen may be driven to control the operation of the light source 11 of the color light therapy device, select a light source pattern, adjust a time, or adjust brightness. The color light therapy program would have been easily understood and implemented in various ways by one of ordinary skill in the art. For example, the color light therapy program may be driven when a color light therapy icon displayed on a wallpaper of the PC or a widget screen of the smartphone is selected, to provide the color light therapy UI screen for controlling the operation of the light source 11, selecting a light source pattern, adjusting a time, or adjusting brightness.

As described above, since visible light is used, a color light therapy device according to the present invention is safe with no side effects. Since a user may use the color light therapy device by connecting a power jack to a mobile phone, a PC, a laptop, a tablet PC, a smartphone, a PDA, a vehicle, or a socket at home while carrying the color light therapy device, anyone may conveniently use the color light therapy device to perform color light therapy on a human body without exchanging or charging a battery.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A color light therapy device comprising:
a body having a hollow space in a center portion thereof, wherein a first side of the hollow space is closed and a second side of the hollow space has a light outlet;
a printed circuit board (PCB) disposed on the first side of the hollow space of the body;
at least one light source disposed on the PCB and configured to emit color light in a given wavelength range to perform color light therapy, wherein the light source includes at least one of a light-emitting diode (LED), an organic light-emitting diode (OLED) and a tricolor LED;
an optical filter covering the light outlet, the optical filter filtering and focusing the color light emitted by the light source and emitting the filtered and focused color light through the light outlet;
a reflector provided inside the hollow space of the body and in a lateral side of the light source to reflect the color light emitted by the light source to the optical filter;

an adhesive element disposed on an outer surface of the body around the light outlet; and a power jack connected to the PCB through an electric wire.

2. The color light therapy device of claim 1, wherein the color light has a visible light wavelength band.

3. The color light therapy device of claim 2, further comprising at least one additional body having the same structure as of the body, wherein the additional body is connected to the power jack through the electric wire.

4. The color light therapy device of claim 2, further comprising a light source operation controller disposed on the body or on the electric wire.

5. The color light therapy device of claim 1, wherein the optical filter is formed of any one of plastic, glass, quartz, crystal, and crystal glass, and is configured such that a light-transmitting surface is cut to have a circular or polygonal shape or convex lens shape.

6. The color light therapy device of claim 5, further comprising at least one additional body having the same structure as of the body, wherein the additional body is connected to the power jack through the electric wire.

7. The color light therapy device of claim 5, further comprising a light source operation controller disposed on the body or on the electric wire.

8. The color light therapy device of claim 1, wherein the reflector is formed of any one of a reflection plate and a reflection film.

9. The color light therapy device of claim 8, further comprising at least one additional body having the same structure as of the body, wherein the additional body is connected to the power jack in parallel with the body through the electric wire.

10. The color light therapy device of claim 8, further comprising a light source operation controller disposed on the body or on the electric wire.

11. The color light therapy device of claim 1, further comprising at least one additional body having the same structure as of the body, wherein the additional body is connected to the power jack in parallel with the body through the electric wire.

12. The color light therapy device of claim 11, further comprising a gender for separation/connection, wherein the gender is configured to connect the body and the additional body and the power jack.

13. The color light therapy device of claim 1, wherein the adhesive element is a double-sided adhesive tape or a hydrogel pad.

14. The color light therapy device of claim 1, further comprising a light source operation controller disposed on the body or on the electric wire.

15. The color light therapy device of claim 14, further comprising at least one additional body having the same structure as of the body, wherein the additional body is connected to the power jack through the electric wire.

16. The color light therapy device of claim 14, wherein the light source operation controller comprises at least one of a light source operation button for turning on or off the light source, a light source pattern button for controlling a light source pattern, a time adjustment button for adjusting a light source operation time and a brightness adjustment button for adjusting light source brightness.

17. The color light therapy device of claim 16, further comprising at least one additional body having the same structure as of the body, wherein the additional body is connected to the power jack in parallel with the body through the electric wire.

18. The color light therapy device of claim 16, wherein the adhesive element is a double-sided adhesive tape or a hydrogel pad.

* * * * *